United States Patent
Boese et al.

(10) Patent No.: US 7,641,650 B2
(45) Date of Patent: Jan. 5, 2010

(54) REMOTE CONTROL DEVICE FOR A MEDICAL PROBE

(75) Inventors: Jan Boese, Eckental (DE); Martin Kleen, Neunkirchen (DE); Marcus Pfister, Erlangen (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 840 days.

(21) Appl. No.: 10/966,754

(22) Filed: Oct. 15, 2004

(65) Prior Publication Data
US 2005/0187538 A1    Aug. 25, 2005

(30) Foreign Application Priority Data
Feb. 25, 2004    (DE) .................. 10 2004 009 135

(51) Int. Cl.
A61B 17/00    (2006.01)
(52) U.S. Cl. ............................ 606/1; 463/38; 600/146
(58) Field of Classification Search .............. 606/1; 600/118, 146–150, 131, 139; 604/95.05; 700/83, 85, 65, 3; 463/37–39
See application file for complete search history.

(56) References Cited

U.S. PATENT DOCUMENTS

| | | | | |
|---|---|---|---|---|
| 4,459,440 A | * | 7/1984 | Wiczer ........................ 200/6 A |
| 4,726,355 A | | 2/1988 | Okada | |
| 4,962,717 A | * | 10/1990 | Tsumiyama ............ 114/144 R |
| 5,389,865 A | | 2/1995 | Jacobus et al. | |
| 5,749,362 A | * | 5/1998 | Funda et al. ................. 600/407 |
| 5,843,017 A | * | 12/1998 | Yoon ........................... 604/22 |
| 5,897,488 A | * | 4/1999 | Ueda ........................... 600/143 |
| 6,113,395 A | * | 9/2000 | Hon ........................... 434/262 |
| 6,154,198 A | * | 11/2000 | Rosenberg .................. 345/161 |
| 6,277,127 B1 | * | 8/2001 | Hasson ....................... 606/130 |
| 6,425,865 B1 | * | 7/2002 | Salcudean et al. ........... 600/437 |
| 6,432,043 B2 | * | 8/2002 | Nakaichi et al. ............ 600/120 |
| 6,459,420 B1 | * | 10/2002 | Harris ........................ 345/161 |
| 6,607,475 B2 | * | 8/2003 | Doyle et al. ................... 600/1 |
| 2002/0120188 A1 | | 8/2002 | Brock et al. | |
| 2002/0177789 A1 | | 11/2002 | Ferry et al. | |
| 2003/0060686 A1 | * | 3/2003 | Taylor et al. ................ 600/210 |
| 2004/0138701 A1 | * | 7/2004 | Haluck ........................ 606/205 |
| 2004/0186345 A1 | * | 9/2004 | Yang et al. .................. 600/102 |
| 2005/0187538 A1 | * | 8/2005 | Boese et al. ................... 606/1 |
| 2005/0228228 A1 | * | 10/2005 | Boulais ....................... 600/131 |

FOREIGN PATENT DOCUMENTS

| | | |
|---|---|---|
| DE | 44 14 809 C2 | 11/1995 |
| WO | WO 98/24017 | 6/1998 |
| WO | WO 01/91100 A1 | 11/2001 |
| WO | WO 03/042957 A1 | 5/2003 |
| WO | WO 03/077101 A2 | 9/2003 |

* cited by examiner

*Primary Examiner*—John P Leubecker
*Assistant Examiner*—Victoria W Chen

(57) ABSTRACT

The device according to the invention ensures accurate and in particular sensitive navigation of the probe, which can be inserted into a body, despite the fact that the remote control uses simple means, by means of a movement (MR;MB;MP) corresponding intuitively to the navigation of a probe using the control device (1). Intuitive operation can be converted in particular using an inventive U-shaped embodiment of the control device (1). Sensitive controllability can be increased by transmitting the mechanical interaction between the probe and an environment under examination to the control device (1) and thus directly to the operating hand (3) by means of inventive feedback.

9 Claims, 1 Drawing Sheet

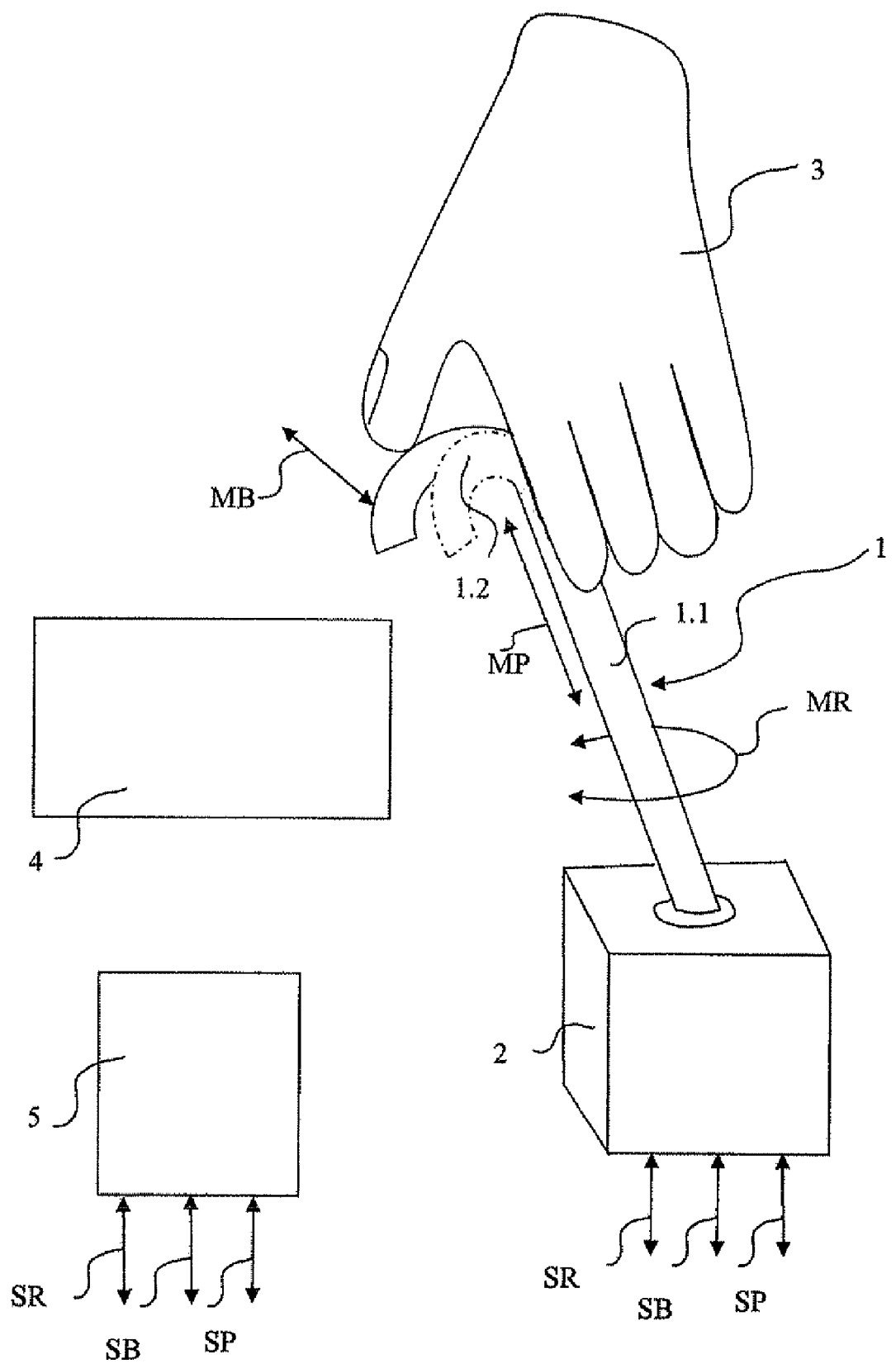

REMOTE CONTROL DEVICE FOR A MEDICAL PROBE

CROSS REFERENCE TO RELATED APPLICATIONS

This application claims priority to the German application No. 10 2004 009 135.8, filed Feb. 25, 2004 and which is incorporated by reference herein in its entirety.

FIELD OF INVENTION

The invention relates to a device for the remote-control navigation by hand of a probe, which can be inserted into a body.

BACKGROUND OF INVENTION

A device of this type is known from the patent application U.S. 2002/0177789 A1.

Internal examinations of the body by means of a probe, which can be inserted into the body from the outside, are one of the standard methods used in diagnostic medicine. For example, catheters inserted from outside the body are used to investigate intravascular diseases and endoscopes are used to examine the bronchi. Generally the doctor is positioned directly adjacent to the patient when per-forming the examination. The probe is navigated by hand within the body by means of visual control or continuous x-ray control, thus resulting in the doctor undertaking the treatment being constantly exposed to radiation. This is one reason why remote-control probes are used in new systems for endoscopic diagnostic and therapy, whereby said probes can be controlled by hand by a doctor from an adjoining room by means of an external control device.

SUMMARY OF INVENTION

A device of this type for the remote-control navigation by hand of a probe, which can be inserted into a body, by means of an external control unit is known from patent application U.S. 2002/0177789 A1. In the aforementioned case the navigation of the probe in the inward direction and the outward direction is ensured by means of a joy-stick. A mechanical tilting movement of the joystick away from the body is converted to electronic control commands by means of a command sensor, such that the probe is moved in the inward direction. A tilting movement of the joystick towards the body is correspondingly converted to control commands, such that the probe is moved in the out ward direction. In order to prevent incorrect operation and thus to protect the patient from serious injury due to incorrect navigation of the probe, it is considered necessary that the navigation movement of the probe corresponding to each tilting movement is identified explicitly by lettering or by a symbol.

An object of the present invention is to create a device, which enables an accurate and in particular sensitive navigation of the probe despite remote control using simple means.

This object is achieved by the claims. Advantageous embodiments of the device are subjects of the dependent claim.

Intuitive operation of the device for the remote control of a probe, which can be inserted into the body, also guarantees reliable and sensitive navigation through the human body without direct visual contact and operational contact, even when the operator and probe are spatially separated. The remote control is thereby operated on the basis of the navigational movements that can be executed by the probe, so that the corresponding navigational movements can be executed even without any specific identifying marking on a control de-vice or addition indications by means of a display.

According to one embodiment according to the invention, sensitive yet simple navigation of the probe can be implemented using only one hand particularly advantageously by means of a U-shaped control de-vice with an almost rigid arm-type component with a bendable, curved component connected thereto, whereby in particular an intuitively executable inward movement and/or rotational movement and/or curving movement of the control device thus configured can be converted to an inward movement and/or a rotational movement and/or a curving movement of the probe corresponding thereto. The curving of the tip of the probe can expediently be adjusted by means of pressure exerted by a hand on the bend of the control device, when the U-shaped component is configured in an elastic manner.

The sensitive controllability of the probe can be very effectively improved by transmitting the mechanical interaction between the probe and the environment to be examined by it as "forced feedback", to the control device and thus to the hand. With the inventive transmission of the mechanical interaction to the control device, the doctor undertaking the treatment obtains important information regarding anatomical data within the local environment around the tip of the probe, whereby the information is received directly by the operating hand. Bifurcation of the blood vessels can be identified for example by a change in movement resistance related to the environment, by means of a rotation with simultaneous curving of the tip of the probe.

In contrast to a known rigid joy stick, user-friendly, sensitive but nevertheless simple operation is guaranteed using the control device thus configured, so that sensitive and thus particularly reliable navigation of the probe can be executed through the body even during a lengthy examination and where there are difficult anatomical conditions, such as extensive blood vessel bifurcation for example.

BRIEF DESCRIPTION OF THE DRAWING

The invention and further embodiments of the invention according to the subclaims are described in more detail below with reference to a schematically illustrated exemplary embodiment in the drawing.

DETAILED DESCRIPTION OF INVENTION

The device represented in the drawing for remote-control navigation comprises a U-shaped, control device 1 that can be operated by hand 3 to execute the mechanical movements (MB;MR;MP) and a command sensor 2 to convert the executed movements to the corresponding navigation control signals (SB;SR;SP) that can be transmitted to the diagrammatically represented remote-control probe 5, which may be inserted into a diagrammatically represented human body 4. The control device comprises an almost rigid arm-type component 1.1 and an elastic, curved component 1.2 connected thereto. Mechanical movements in the form of an inward movement MP, rotational movement MR and a curving movement MB can be executed using the control device 1.

Each specific mechanical movement MR, MB and MP is thereby assigned a corresponding scaled navigational movement of the probe, whereby the assignment is based on the types of movement of the control device 1, resulting in intuitive, user-friendly operation. The inward adjustment of the remote-control probe can be controlled by means of an inward movement MP parallel to the axis of the arm-type component 1.1, whilst rotational adjustment can be predefined to a defined angle of the probe by means of a rotational movement MR about the axis of the arm-type component 1.1. The curving movement of a probe can be controlled in this embodiment by means of the elastic bending of the curved component 1.2 of the control device 1. Pressure exerted by the hand 3 and converted to a curving movement MB causes the curved component 1.2 of the control device to curve in the direction of the position indicated by the broken line, adjusting the position of the probe, which can be inserted into the body, on the basis of the curve. The original starting position of the elastically configured curved component 1.2 and thus also the remote-control probe is resumed when the pressure on the control device 1 is released with a corresponding intuitive hand movement. All the mechanical movements (MB;MR;MP), which can be converted by the control device 1, can be executed independently of each other, thus guaranteeing a high level of sensitivity during the navigation of the probe through a human body. In addition to control of the inward, rotational and curving movements (MB;MR;MP) of the probe as mentioned here, other types of movement such as a gripping movement for example can be controlled in an intuitive manner by means of further embodiments of the control device 1 according to the invention.

The mechanical movements (MB;MR;MP) executed by the hand 3 and transmitted to the control device 1 are converted by means of the command sensor 1 to navigation control signals (SB;SR;SP), and are transmitted to the spatially remote probe. The control device 1 is connected to the command sensor 2, in such a way that it can be moved in the direction of the inward movement MP and can be rotated about the axis of the arm-type component 1.1. The mechanical movements of the probe are converted in such a manner that the navigation control signal SP is assigned to an inward movement MP, the navigation control signal SR is assigned to a rotational movement MR and the navigation control signal SB is assigned to a curving movement MB. The distance the probe moves, known as the first distance, is represented by a movement of the control stick which is scaled, and shorter, known as the second distance. This provides for information about the environment local at the tip of the probe to be transmitted back to the command sensor, the control device, and ultimately, the doctor's hand. Transmission of the navigation control signals (SB;SR;SP) between the control device 1 and a probe can take place in both a wired and a wireless manner, for example via the internet or a WLAN or an infrared connection to the probe. Depending on the structure of the remote-control probe, the control signals are converted for example to electrical or mechanical signals to control magnetic fields, motors or other navigational means, and are thus converted to a movement corresponding to the control signal.

The main idea behind the invention can be summarized as follows:

Despite the fact that the remote control uses simple means, the de-vice according to the invention ensures accurate and in particular sensitive navigation of the probe, which can be inserted into a body, by means of a movement (MR;MB:MP) using the control device (1) corresponding intuitively to the navigation of a probe. Intuitive operation can be converted in particular using an inventive U-shaped embodiment of the control device (1). Sensitive controllability can be increased by means of an inventive feeding back of the mechanical interaction between the probe and the environment under examination to the control device (1) and thus directly to the operating hand (3).

The invention claimed is:

1. A remote control device for remotely controlling a medical probe, comprising:
    a manually operable control stick comprising an elongated portion and a bendable curved handle, for inputting a navigation command by moving the control stick, and for adjusting the curving of a tip of the medical probe relative to an elongated portion of the medical probe by bending the curved handle;
    a command sensor operatively connected to the control stick adapted to:
        convert the navigation command into a navigation control signal for navigating the medical probe, and
        move the control stick in a manner similar to a movement of the medical probe,
    wherein the elongated portion of the control stick is solid, and the handle is U-shaped,
    wherein U-shaped handle is elastic,
    wherein the U-shaped handle is adapted to bend when a force is applied to the handle, and
    wherein the U-shaped handle is further adapted to return to its original shape after the force is no longer applied.

2. The control device according to claim 1, wherein the navigation command includes a linear forward movement of the control stick relative to a travel direction of the medical probe.

3. The control device according to claim 1, wherein the navigation command includes a rotary motion of the control stick for adjusting a rotation angle of the medical probe.

4. The control device according to claim 1, wherein in the medical probe is capable of being inserted into a human body.

5. The control device according to claim 4, wherein the control stick is moved parallel to a navigation direction of the medical probe.

6. The control device according to claim 5, wherein the movement of the control stick and the movement of the medical probe are to scale.

7. The control device according to claim 5, wherein a first travel distance of the medical probe is converted into a second travel distance of the control stick, and the second travel distance is shorter than the first travel distance.

8. The control device according to claim 1, wherein the command sensor is adapted to convert a plurality of mechanical movements of the control stick into a plurality of corresponding electrical navigation control signals for navigating the medical probe.

9. The control device according to claim 1, wherein the command sensor is adapted to simulate a mechanical interaction between the medical probe inserted into an examination environment and the examination environment by moving the control stick according to a forced feedback mechanism.

* * * * *

UNITED STATES PATENT AND TRADEMARK OFFICE
CERTIFICATE OF CORRECTION

| | | |
|---|---|---|
| PATENT NO. | : 7,641,650 B2 | Page 1 of 1 |
| APPLICATION NO. | : 10/966754 | |
| DATED | : January 5, 2010 | |
| INVENTOR(S) | : Boese et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1097 days.

Signed and Sealed this

Sixteenth Day of November, 2010

David J. Kappos
*Director of the United States Patent and Trademark Office*